United States Patent
Kuo et al.

(10) Patent No.: US 6,790,977 B2
(45) Date of Patent: Sep. 14, 2004

(54) PROCESS FOR PREPARING 3,4-DIHYDROXY-BENZONITRILE

(75) Inventors: Lung-Huang Kuo, Taichung (TW); Dei-She Ke, Taichung (TW); Chih-Da Lin, Taichung (TW); Shyh-Shyan Jwo, Taichung (TW); Wen-Hsin Chang, Taichung (TW)

(73) Assignee: Sinon Corporation, Taichung (TW)

( * ) Notice: Subject to any disclaimer, the term of this patent is extended or adjusted under 35 U.S.C. 154(b) by 0 days.

(21) Appl. No.: 10/209,401

(22) Filed: Jul. 30, 2002

(65) Prior Publication Data

US 2004/0024239 A1 Feb. 5, 2004

(51) Int. Cl.$^7$ .............................................. C07C 255/50
(52) U.S. Cl. ....................................................... 558/423
(58) Field of Search ........................................... 558/423

(56) References Cited

U.S. PATENT DOCUMENTS

| | | | |
|---|---|---|---|
| 4,339,462 A | * 7/1982 | Muntwyler et al. | ......... 514/721 |
| 6,410,538 B2 | * 6/2002 | Nakagawa et al. | .... 514/252.01 |
| 6,573,397 B2 | * 6/2003 | Shirai et al. | ................. 558/423 |

FOREIGN PATENT DOCUMENTS

WO    WO 2004/013094 A2 *  2/2004

\* cited by examiner

*Primary Examiner*—Joseph K. McKane
*Assistant Examiner*—Ebenezer Sackey
(74) *Attorney, Agent, or Firm*—Darby & Darby

(57) ABSTRACT

A process for preparing 3,4-dihydroxybenzonitrile includes the steps of reacting a nitrile compound with an alkali metal halide, followed by treating with an acid.

8 Claims, No Drawings

PROCESS FOR PREPARING 3,4-DIHYDROXY-BENZONITRILE

BACKGROUND OF THE INVENTION

1) Field of the Invention

The present invention relates to a process for preparing 3,4-dihydroxybenzonitrile.

2) Description of the Related Art 3,4-dihydroxybenzonitrile is an important starting material for the preparation of a number of valuable chemical compounds, including thiazole, 2-oxazolines, tetraazoles, imidazole, triazoles, and benzamidines. Several conventional processes for preparing 3,4-dihydroxybenzonitrile have been known for a long time. For example, in *Tetrahedron Letters* 1978, 52, 5183–5186, McCarthy et al. reported a process for preparing 3,4-dihydroxybenzonitrile by heating 3,4-dimethoxybenzonitrile in dimethyl formamide (DMF) in the presence of an excess amount of sodium cyanide at 180° C. for 24 hours with a yield of 44%. Hwu et al. (*J. Org. Chem.* 1997, 62, 4097–4104) described a process for the preparation of 3,4-dihydroxybenzonitrile by heating 3,4-dimethoxybenzonitrile in a mixture of tetrahydrofuran (THF) and 1,2-dimethyl-2-imidazolidinone (DMEU) in the presence of either sodium bis(trimethylsilyl)amide [NaN(SiMe$_3$)$_2$] or lithium diisopropylamide [LiN(Pr$^i$)$_2$] at 185° C. for 12 hours in a sealed tube. In this case, an excess amount of lithium diisopropylamide [LiN(Pr$^i$)$_2$] will be required for a higher yield of 3,4-dihydroxybenzonitrile. Accordingly, Hwu et al. (*Synthesis* 1998, 329–332) further reported a process for the preparation of 3,4-dihydroxybenzonitrile by heating methyl 3,4-dimethoxybenzoate in a mixture of tetrahydrofuran (THF) and 1,2-dimethyl-2-imidazolidinone (DMEU) in the presence of either sodium bis(trimethylsilyl)amide [NaN(SiMe$_3$)$_2$] or lithium diisopropylamide [LiN(Pr$^i$)$_2$] at 185° C. for 24 hours in a sealed tube with a yield of 63%.

Further, Feng and co-workers (*Synthetic Communications* 1998, 28(20):3765–3768) reported a process for preparing 3,4-dihydroxybenzonitrile by microwave irradiating 3,4-dihydroxybenaldehyde with hydroxyammonium salt in the presence of HCOOH/SiO$_2$ with a yield of 70%. By using N-methylpyrrolidinone (NMP) under microwave irradiation, Chakraborti and co-worker (*Tetrahedron* 1999, 55, 13265–13268) reported that an improved yield of 89% can be achieved.

However, the aforementioned processes for preparing 3,4-dimethoxybenzonitrile are less than fully satisfactory in view of low yields of product, expensive starting material and solvents, and hazardous reagents, thereby limiting their use in commercial scale production.

SUMMARY OF THE INVENTION

Therefore, it is an object of this invention to provide a process for the preparation of 3,4-dihydroxybenzonitrile particularly characterized by high yield and a low cost starting material.

According to one aspect of this invention, the process for preparing 3,4-dihydroxybenzonitrile comprises the steps of reacting a nitrile compound of formula (I)

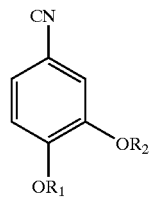

I wherein R$_1$ and R$_2$ are independently selected from the group consisting of H and C$_1$–C$_4$ alkyl with the proviso that R$_1$ and R$_2$ can not be H at the same time, or R$_1$ and R$_2$ may taken together to form —CH$_2$—, with an alkali metal halide in the presence of a solvent and followed by treating with an acid to produce 3,4-dihydroxybenzonitrile.

According to another aspect of this invention, the process for preparing 3,4-dihydroxybenzonotrile comprises the steps of converting an aldehyde compound of formula (II)

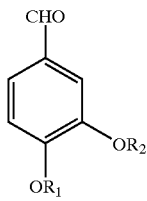

II into a nitrile compound of formula (I)

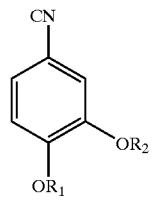

I wherein R$_1$ and R$_2$ independently represent H or a C$_1$–C$_4$ alkyl group, with the proviso that R$_1$ and R$_2$ can not be H at the same time, or R$_1$ and R$_2$ may taken together to form —CH$_2$—; reacting the nitrile compound with an alkali metal halide compound in the presence of a solvent; and followed by treating with an acid to produce 3,4-dihydroxybenzonitrile.

DETAILED DESCRIPTION OF THE INVENTION

The process of this invention for preparing 3,4-dihydroxybenzonitrile includes the steps of: (a) converting an aldehyde compound of formula (II)

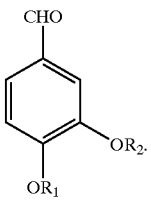

II into a nitrile compound of formula (I)

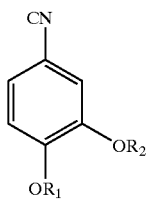

wherein $R_1$ and $R_2$ independently represent H or a $C_1$–$C_4$ alkyl group, with the proviso that $R_1$ and $R_2$ can not be H at the same time, or $R_1$ and $R_2$ may taken together to form —$CH_2$—; (b) reacting the nitrile compound obtained from step (a) with an alkali metal halide compound in the presence of a solvent; and (c) followed by treating with an acid to produce 3,4-dihydroxybenzonitrile.

Preferably, in formula (I), $R_1$ and $R_2$ are independently selected from a group consisting of methyl and ethyl.

In the preferred embodiments, the alkali metal halide compound is selected from a group consisting of lithium bromide, lithium chloride, sodium iodide and potassium iodide. Preferably, the alkali metal halide compound is lithium bromide.

Preferably, suitable solvent for use in the process of the present invention is dimethyl formamide (DMF).

Preferably, reaction of the nitrile compound of formula (I) with the alkali metal halide compound is carried out at a temperature in a range of 160–180° C. for 10 hours.

The present invention will be further illustrated via the following examples, which should not be construed to limit this invention.

EXAMPLES

Example 1a

Preparation of 3-methoxy-4-hydroxy benzonitrile

To a 3-necked 500 mL round bottom flask equipped with a mechanical stirrer and a condenser, 3-methoxy-4-hydroxy benzoaldehyde (50.2 g, 0.33 mole), hydroxylamine hydrochloride (25.5 g, 0.37 mole), and N,N'-dimethylformamide (40 mL) were successively added at 25° C., followed by heating in an oil bath at 140° C. for 1 hour. The reaction mixture was allowed to cool to 85° C., and water (250 mL) was added to yield 3-methoxy-4-hydroxybenzonitrile. The reaction mixture was further cooled to 10° C. for a complete precipitation, and the resulting solid was then isolated by filtration and dried under reduced pressure to yield a product as an off-white solid with a yield of 95% and a purity of higher than 99% as indicated by HPLC analysis.

Example 1b

Preparation of 3,4-Dimethoxybenzonitrile

Conversion of 3,4-dimethoxybenzoaldehyde into a corresponding nitrile compound was carried out according to the process of Example 1a to yield 3,4-dimethoxybenzonitrile as an off-white solid with a yield of 95% and a purity of higher than 99% as indicated by HPLC analysis.

Example 1c

Preparation of 3-Ethoxy-4-hydroxybenzonitrile

Conversion of 3-Ethoxy-4-hydroxybenzoaldehyde into a corresponding nitrile compound was carried out according to the process of Example 1a to yield 3-Ethoxy-4-hydroxy benzonitrile as a pale brown solid with a yield of 95% and a purity of higher than 97% as indicated by HPLC analysis.

Example 1d

Preparation of 3,4-diethoxybenzonitrile

Conversion of 3-Ethoxy-4-hydroxybenzoaldehyde into a corresponding nitrite compound was carried out according to the process of Example 1a to yield 3,4-diethoxybenzonitrile as a yellow solid with a yield of 92% and a purity of higher than 93% as indicated by HPLC analysis.

Example 1e

Preparation of 3,4-(methylene)benzonitrile

Conversion of 3,4-(methylene)benzoaldehyde into a corresponding nitrile compound was carried out according to the process of Example 1a to yield 3,4-(methylene) benzonitrile as a pale brown solid with a yield of 94% and a purity of higher than 97% as indicated by HPLC analysis.

Example 2a

Preparation of 3,4-dihydroxybenzonitrile from 3-methoxy-4-hydroxybenzonitrile

To a 4-necked 1 L round bottom flask equipped with a mechanical stirrer and a condenser, 3-methoxy-4-hydroxybenzonitrile 2a (70.7 g, 0.47 mole), lithium bromide (81.3 g, 0.94 mole), and N,N'-dimethylformamide (220 mL) were added successively at 25° C., followed by heating in an oil bath at 180° C. for 10 hours. The reaction mixture was allowed to cool to 85° C. Water (285 mL) was then added, and upon cooling to 25° C., and treatment with concentrated hydrochloric acid proceed. The resulting mixture was extracted with ethyl acetate (300 mL×2). The extract was concentrated under reduced pressure to give a pale brown solid. Water (430 mL) was added and the mixture was then heated till the mixture became homogeneous. After the reaction mixture was cooled down to approximately 40° C., 3,4-Dihydroxybenzonitrile was precipitated out and the reaction mixture was further cooled to 10° C. so as to ensure complete precipitation. The resulting solid was isolated by filtration and dried under reduced pressure. 3,4-Dihydroxybenzonitrile (42.5 g) was obtained as a white solid with a yield of 67% and a purity of greater than 99% as indicated by HPLC analysis.

Example 2b

Preparation of 3,4-dihydroxy benzonitrile from 3,4-Dimethoxybenzonitrile

The preparation was carried out according to the process of Example 2a except that 3,4-Dimethoxybenzonitrile was used as the starting material instead of 3-methoxy-4-hydroxybenzonitrile, and 2-fold of lithium bromide (162.6 g, 1.88 mole) were added to form the reaction mixture. 3,4-Dihydroxybenzonitrile was obtained as a white solid with a yield of 65% and a purity of greater than 98% as indicated by HPLC analysis.

Example 2c

Preparation of 3,4-dihydroxy benzonitrile from 3-ethoxy-4-hydroxy benzonitrile

The preparation was carried out according to the process of Example 2a except that 3-ethoxy-4-hydroxybenzonitrile was used as the starting material instead of 3-methoxy-4-hydroxybenzonitrile. 3,4-Dihydroxybenzonitrile was obtained as a white solid with a yield of 79% and a purity of greater than 98% as indicated by HPLC analysis.

Example 2d

Preparation of 3,4-dihydroxybenzonitrile from 3,4-diethoxybenzonitrile

The preparation was carried out according to the process of Example 2a except that 3,4-diethoxybenzonitrile was used as the starting material instead of 3-methoxy-4-hydroxybenzonitrile, and 2-fold of lithium bromide (162.6 g, 1.88 mole) were added to form the reaction mixture. 3,4-Dihydroxybenzonitrile was obtained as a white solid with a yield of 79% and a purity of greater than 92% as indicated by HPLC analysis.

Example 2e
Preparation of 3,4-dihydroxybenzonitrile from 3,4-(methylenedioxy)benzonitrile The preparation was carried out according to the process of Example 2a except that 3,4-(methylenedioxy)benzonitrile was used as the starting material instead of 3-methoxy-4-hydroxybenzonitrile to form the reaction mixture. 3,4-Dihydroxybenzonitrile was obtained as a pale brown solid with a yield of 94% and a purity of greater than 97% as indicated by HPLC analysis.

Example 3a
Preparation of 3,4-dihydroxybenzonitrile by reacting with lithium chloride To a 3-necked 250 mL round bottom flask equipped with a mechanical stirrer and a condenser, 3-methoxy-4-hydroxybenzonitrile (13.4 g, 89.9 mmole), lithium chloride (7.6 g, 179.2 mmole), and N,N'-dimethylformamide (60 mL) were added successively at 25° C., followed by heating in an oil bath at 180° C. for 20 hours. The reaction mixture was allowed to cool to 85° C. Water (285 mL) was then added, and upon cooling to 25° C., treatment with concentrated hydrochloric acid proceed. The resulting mixture was extracted with ethyl acetate (300 mL×2). The extract was concentrated under reduced pressure to give a pale brown solid. Water (430 mL) was added and the mixture was then heated till the mixture became homogeneous. After the reaction mixture was cooled down to approximately 40° C., 3,4-Dihydroxybenzonitrile was precipitated out and the reaction mixture was further cooled to 10° C. so as to ensure complete precipitation. The resulting solid was isolated by filtration and dried under reduced pressure. 3,4-Dihydroxybenzonitrile was obtained as a white solid with a yield of 70.6% and a purity of greater than 99% as indicated by HPLC analysis.

Example 3b
Preparation of 3,4-dihydroxybenzonitrile by reacting with sodium iodide The preparation was carried out according to the process of Example 3a except that sodium iodide was used instead of lithium bromide. 3,4-Dihydroxybenzonitrile was obtained as a white solid with a yield of 58% and a purity of greater than 99% as indicated by HPLC analysis.

Example 3c
Preparation of 3,4-dihydroxybenzonitrile by reacting with potassium iodide The preparation was carried out according to the process of Example 3a except that potassium iodide was used instead of lithium bromide. 3,4-Dihydroxybenzonitrile was obtained as a white solid with a yield of 85.2% and a purity of greater than 99% as indicated by HPLC analysis.

While the invention has been described with reference to the above detailed description and the preferred examples, it is not intended to be limited thereto. It will be apparent to those skilled in the art that numerous modifications and variations can be made in the light of the disclosed techniques and the examples of the present invention. It is therefore intended that simple variations and modifications made according to the appended claims and specification of the present invention without departing from the spirit of the present invention should be covered within the scope of the present invention.

We claim:

1. A process for preparing 3,4-dihydroxybenzonitrile, comprising the steps of:

(a) reacting a nitrile compound of formula (I)

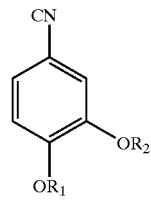

I wherein

R1 and R2 independently represent H or a C1–C4 alkyl group, with the proviso that $R_1$ and $R_2$ can not be H at the same time, or R1 and R2 may taken together to form $CH_2$, with an alkali metal halide compound in the presence of a solvent; and (b) followed by treating with hydrochloric acid to produce 3,4-dihydroxybenzonitrile.

2. The process of claim 1, wherein R1 is H and R2 is methyl.

3. The process of claim 1, wherein both R1 and R2 are methyl.

4. The process of claim 1, wherein R1 is H and R2 is ethyl.

5. The process of claim 1, wherein both R1 and R2 are ethyl.

6. The process of claim 1, wherein R1 and R2 taken together represent a methylene moiety.

7. The process of claim 1, wherein the alkali metal halide compound is selected form a group consisting of lithium bromide, lithium chloride, sodium iodide and potassium iodide.

8. The process of claim 1, wherein the solvent is N,N'-dimethyl formamide.

* * * * *